United States Patent [19]
Morikawa et al.

[11] Patent Number: 5,405,759
[45] Date of Patent: Apr. 11, 1995

[54] HEPARITINASE, PROCESS FOR PRODUCING THE SAME AND BACTERIA PRODUCING THE SAME

[75] Inventors: Kiyoshi Morikawa, Hinode; Hirofumi Miyazono; Hiroshi Maruyama, both of Higashiyamato; Keiichi Yoshida, Higashimurayama, all of Japan

[73] Assignee: Seikagaku Kogyo Kabushiki Kaisha, Japan

[21] Appl. No.: 154,740

[22] Filed: Nov. 18, 1993

Related U.S. Application Data

[62] Division of Ser. No. 843,812, Feb. 28, 1992, Pat. No. 5,290,695.

[30] Foreign Application Priority Data

Mar. 6, 1991 [JP] Japan ................................. 3-63707

[51] Int. Cl.$^6$ .......................... C12N 1/00; C12N 9/00; C12N 9/52; C12N 9/54
[52] U.S. Cl. ..................................... 435/71.1; 435/13; 435/71.2; 435/170; 435/835; 435/183; 435/209; 435/220; 435/221
[58] Field of Search ............... 435/209, 220, 221, 835, 435/231, 13, 71.1, 71.2, 170, 183

[56] References Cited

FOREIGN PATENT DOCUMENTS

| | | | |
|---|---|---|---|
| 370958 | 5/1990 | European Pat. Off. | C12N 9/88 |
| 1132381 | 5/1989 | Japan | C12N 9/88 |
| 3247297 | 11/1991 | Japan | C12P 19/26 |

OTHER PUBLICATIONS

Nakamura, et al. J. Clinical Microbiology vol. 26 No. 5 May 1988 pp. 1070–1071.
Karbassi, et al. Can. J. Microbiology vol. 26 No. 3 1980 pp. 377–384.
Linhardt, et al. Applied Biochemistry & Biotechnology vol. 12, No. 2 Apr. 1986 pp. 135–136.

*Primary Examiner*—Michael G. Wityshyn
*Assistant Examiner*—Jane A. Williams
*Attorney, Agent, or Firm*—Bierman and Muserlian

[57] ABSTRACT

Disclosed are novel enzymes, heparitinase T-I, heparitinase T-II, heparitinase T-III and heparitinase T-IV, which degrade heparan sulfate and/or heparin, a process for producing thereof by cultivating a novel *Bacillus circulans* HpT 298 having an ability of producing these enzymes and a novel *Bacillus circulans* HpT 298.

2 Claims, 7 Drawing Sheets

HEPARITINASE T-I/T-II
(SUBSTRATE: HEPARAN SULFATE)

HEPARITINASE T-II
(SUBSTRATE: HEPARAN SULFATE)

HEPARITINASE T-IV
(SUBSTRATE: HEPARAN)

PEAK  1: ΔDiHS-OS  2: ΔDiHS-NS  3: ΔDiHS-diN,6S
4: ΔDiHS-diU,NS  5: ΔDiHS-triS

HEPARITINASE, PROCESS FOR PRODUCING THE SAME AND BACTERIA PRODUCING THE SAME

This application is a division of U.S. patent application Ser. No. 843,812 filed Feb. 28, 1992, now U.S. Pat. No. 5,290,695.

BACKGROUND OF THE INVENTION

This invention relates to novel heparitinases which degrade heparan sulfate or heparin, a process for preparing the same and bacteria producing the same.

Heparitinase is a group of enzymes which cleave glucosaminide linkages into heparan sulfate (hereinafter abbreviated to as "HS") and/or heparin (hereinafter abbreviated to as "Hep") which are heteropolysaccharide composed of repeating disaccharide units of N-acetyl-D-glucosamine and uronic acid as a basic structure, and are available as a reagent for analyzing HS or Hep in body or investigating these substances in vivo. Also, in recent years, it has attracted attention due to its availability as an agent used to prepare low molecular weight heparin which is now being developed as an antithrombic agent, or a material (Hep removing agent) for decreasing undesirable side effects of Hep which becomes a problem in therapy using an extracorporeal circulation apparatus. Thus, it can be expected to be used for various purposes for diagnosis and curing.

Heparitinase which can be used for the above use is required to have various properties such as different substrate specificity which recognizes the difference in saccharide chain structure such as the presence or absence, and a bonded position of a sulfate group, and it is desired to be supplied as an enzyme source stably with a large amount. Beginning from this point, the inventors ask for researched on an enzyme which satisfies the above requirements from microorganism origin, investigated bacteria which produce said enzyme and already found three kinds of heparitinases from bacteria belonging to Flavobacterium (Japanese Provisional Patent Publication No. 57183/1990).

As a report referred to in detail purification and properties of heparitinase which is microorganism origin, there have been known, in addition to the above, enzymes isolated from bacteria belonging to Flavobacterium or Bacillus, and disclosed in, for example, Summary of 10th International Glycoconjugate Symposium (p. 330, 1989) or Japanese Provisional Patent Publication No. 142470/1990. These known enzymes are available for the above objects, but it has been further demanded to obtain a novel heparitinase having different substrate specificity in order to accomplish the above objects.

SUMMARY OF THE INVENTION

The present inventors have widely searched bacteria producing novel heparitinases for the reason as mentioned above, and as the results, they have found that Bacillus circulans HpT 298 isolated from a soil in Saitama Prefecture of Japan has an ability of producing novel heparitinases.

These heparitinases are separated and purified to isolate four kinds of novel heparitinases having different properties or substrate specificity with each other. The present invention was made in order to solve the above problems and relates to novel enzymes which degrade HS or Hep, heparitinase T-I, heparitinase T-II, heparitinase T-III and heparitinase T-IV (hereinafter referred to as "enzymes of the present invention"), relates to a process for producing the enzymes of the present invention from bacteria belonging to Bacillus having an ability to produce the enzymes of the present invention efficiently, and also relates to bacteria per se belonging to Bacillus having an ability to produce the enzymes.

DESCRIPTION OF THE PREFERRED EMBODIMENTS

Figure 1:
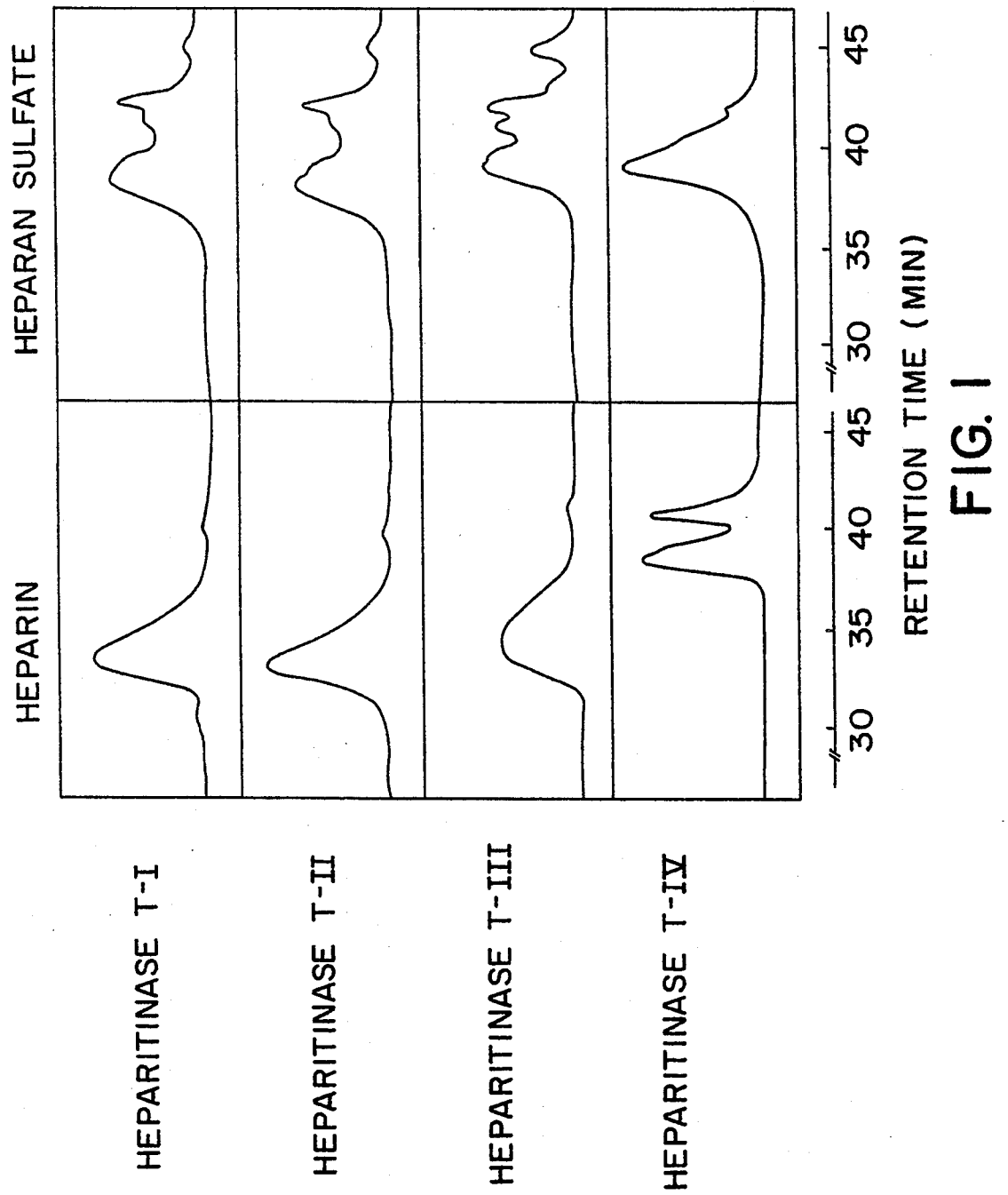
FIG. 1 shows degradation ability of each enzyme against heparin (derived from porcine intestine mucosa) and heparan sulfate (derived from bovine kidney)

In the following, the present invention will be explained in more detail.

Microorganism to be used for producing the enzymes of the present invention, any strains of bacteria belonging to Bacillus and having an ability of producing the enzymes of the present invention may be used, and Bacillus circulans Hpt 298 used in the Examples of the present invention is a novel strain isolated from a soil in Saitama Prefecture of Japan according to investigation of Hep assimilating bacteria by the present inventors', and its bacterial properties are as follows:

(A) Morphological properties
  Gram stain: Negative
  Shape: Rods (0.4 to 0.5 $\mu$m $\times$ 2.0 to 3.6 $\mu$m)
  Spores: Terminal, Ellipsoidal
  Sporangium swollen: Positive
  Paraspore crystal: Negative
  Mobility: Positive
(B) Growth characteristics
  Aerobic growth: Positive
  Anaerobic growth: Negative
  Growth temperature 15° C.: Positive 20° C.: Positive 30° C.: Positive 40° C.: Positive 50° C.: Positive 51° C.: Positive 52° C.: Negative
  Growth in the presence of lysozyme (0.001%): Positive
  Growth in the presence of NaCl 2%: Positive 5%: Negative 7%: Negative
  Growth at pH 6.8 (nutrient broth): Positive
  Growth at pH 5.7 (Sabouraud dextrose broth or agar): Positive
  Growth pH: 5.0 to 9.0, particularly 6.5 to 7.5 are optimum
  Requirement for NaCl and KCl: Negative
(C) Physiological properties and other properties
  Catalase: Positive
  Voges-Proskauer (V-P) test: Negative
  pH at V-P broth: 6.0 or less
  Acid formation from
    D-glucose: Positive
    D-xylose: Positive
    D-mannose: Positive
    L-alabinose: Positive
    D-mannitol: Positive
    sorbitol: Negative
  Gas formation from D-glucose: Negative
  Formation of indole: Negative
  Hydrolysis of casein: Negative Hydrolysis of starch: Positive
Degradation of tyrosine: Negative
Deamination of phenylalanine: Negative
Reduction of nitrate to nitrite: Positive
Utilization of citric acid: Positive
Utilization of propionic acid: Positive
Utilization of heparin: Positive
Utilization of heparan sulfate: Positive
Utilization of chondroitin sulfate: Positive
Utilization of keratan sulfate: Negative
Guanine+Cytosine (G+C) content: 53.0 mole %
Main isoprenoids quinone: menaquinone-7 (MK-7)
Diaminopimelic acid (DAP) in peptidoglycan of cell wall: meso-DAP When the taxonomic position of strain HpT 298 having the above bacterial properties is investigated by referring to Bergey's Manual of Systematic Bacteriology, First Edition, vol. 2 (1986), this bacterium forms endospores and is aerobic gram negative rods having mobility, main isoprenoids quinone of which is menaquinone-7 and contains mesodiaminopimelic acid in peptidoglycan of cell wall so that it can be judged to be a strain belonging to Bacillus. Further, when the other properties thereof are compared to those of known species of Bacillus, this strain can be identified to belong to a species of *Bacillus circulans*. However, known strains of *Bacillus circulans* such as IFO 2, IFO 13635 and IFO 13636 do not produce the enzyme of this invention and thus the strain of the present invention is novel one differentiated from these known strains.

As bacteria which produce degradation enzyme of HS or Hep belonging to Bacillus, there has been known Bacillus sp. BH100 (Japanese Provisional Patent Publication No. 142470/-1990), but as clearly seen from the difference in property of growth under anaerobic condition, maximum growth temperature, pH at V-P broth, and hydrolysis ability of starch and G+C content in DNA therefrom, the above strain HpT 298 is different from strain BH 100. The above strain HpT 298 has been deposited as a deposit number of FERM BP-3765 at the Fermentation Research Institute (FRI), the Agency of Industrial Science and Technology of Japan as International Deposit Authority under the Budapest Treaty. FRI address 1-3, Higashi, 1-Chrome, Tsuduba-shi, Ibaroki-ken, Japan (Zip Code: 305) deposited Feb. 25, 1992.

The novel heparitinase T-I, heparitinase T-II, heparitinase T-III and heparitinase T-IV of the present invention can be obtained by culturing *Bacillus circulans* HpT 298 or bacterium which has ability to produce the enzyme of the present invention and belonging to Bacillus in a nutrient medium to be used for usual cultivation of microorganisms, preferably in a medium to which Hep or HS, or a substance containing the above are added in order to heighten enzyme productivity so that the enzyme is produced and accumulated in a medium or in bacterial cells, which can be separated and purified by the known method to give purified enzyme.

When the above is explained in more detail, bacteria which produce the enzymes of the present invention and belonging to Bacillus are cultured in a suitable nutrient medium, for example, a medium containing a suitable carbon source, nitrogen source, inorganic salts and Hep or HS, or a substance containing the above, and the enzymes of the present invention is produced and accumulated in the medium or in bacterial cells. As the carbon source, any material which can be assimilated may be used, and there may be mentioned, for example, D-glucose, D-xylose, D-mannose, L-alabinose, D-mannitol, starch or hydrolyzate thereof, molasses, a citrate and various kinds of peptones. As the nitrogen source, there may be utilized organic or inorganic nitrogen compounds such as yeast extract, malt extract, various kinds of peptones, various kinds of meat extracts, soybean powder, defatted soybean powder, corn steep liquor, amino acids solution or an ammonium salt, or a material containing the above. As the inorganic salt, there may be used various phosphates, salts of magnesium, potassium, sodium or calcium. If necessary, various kinds of inorganic materials or organic materials which are required for growth of bacteria or production of the enzymes, for example, a defoaming agent such as a silicone oil, a sesame oil or various kinds of surfactants, or vitamins may be added to the medium.

In the present invention, when Hep or HS, or a substance containing the above is added to the medium as an inducer of the enzymes of the present invention, a large amount of the enzymes of the present invention can be formed. Addition of these inducers may be carried out at initiation of the culturing or in the course of cultivation. When these substances are added generally in an amount of 0.2% to 2% in terms of Hep or. HS, good results can be obtained.

Cultivation may be carried out in liquid culture or in solid culture, but generally liquid cultivation is suitable and it is industrially advantageous to carry out submerged culture. Cultivation of the present invention may be carried out by selecting and controlling suitable conditions which are most advantageous for producing the enzymes of the present invention. Cultivation temperature may be optionally changed in the range of 15° to 51° C., but particularly preferred is in the range of 40° to 45° C. Cultivation time may vary depending on the cultivation conditions, but it is generally 1 to 2 days and cultivation may be terminated at the time when amounts of the enzymes of the present invention accumulated become maximum. pH of the medium may be about neutral when the medium is prepared and generally it is not particularly necessary to control.

From both of a supernatant of the culture broth thus obtained and/or an extract of bacterial cells, the above mentioned four kinds of enzymes can be obtained. As for the supernatant of culture broth, ammonium sulfate is added to the supernatant to make 60% saturation, and after dialyzing precipitates formed, enzymes are separated and purified by chromatographic methods using hydroxyapatite, an ion exchange resin, a gel filtering medium and so on. Also, as for enzymes in bacterial cells, the cells are suspended in a suitable buffer and destroyed by an ultrasonic or mechanical crushing to extract enzymes and then centrifuged. Then, the supernatant of the centrifuged extract is subjected to the same procedures used in the above supernatant of culture broth so that purified enzymes can be obtained. However, the present invention is not particularly limited by these purification methods.

The activity of these enzymes can be obtained by measuring increase in ultraviolet absorption, i.e. based on the fact that these enzymes of the present invention are each lyase which acts on glucosaminide linkages and cleaves them to form double bonds between 4-position and 5-position carbon atoms of the uronic acids of non-reducing ends, and double bonds formed absorb ultraviolet ray.

As a substrate of the enzyme, HS derived from bovine kidney is used as for heparitinase T-I, heparitinase T-II and heparitinase T-III and Hep derived from porcine intestine mucosa is used as for heparitinase T-IV.

That is, to 25 μl of an aqueous solution containing 10 mg/ml of the above substrate were added 10 μl of an enzyme solution, 25 μl of 100 mM Tris-acetate buffer (pH 7.0), 25 μl of 20 mM calcium chloride and 15 μl of water, and the mixture is reacted at 45° C. for 10 minutes. To the mixture is added 500 μl of 0.06 N hydrochloric acid solution to stop the reaction and ultraviolet absorption A at 232 nm is measured. As a control, ultraviolet absorption $A_0$ of the same solution at zero (0) time is measured.

One unit is defined as the quantity of the enzyme that catalyzes to form 1 μmole of degraded product from the substrate per minute under the above conditions, and an enzyme activity can be calculated by the following formula:

$A-A_0/5.5$ (mole correction using molecular absorption coefficient) $\times 600/10$ (correction of enzyme dilution) $\times 1/10$ (correction per one minute) = U/ml (unit per 1 ml of enzyme used)

Properties of the novel heparitinases of the present invention are shown below.

(1) Action

Each of the enzymes is a lyase which acts on glucosaminide linkages of Hep or H$ and cleaves them to form double bonds between 4-position and 5-position carbon atoms of uronic acids.

Figure 2A:
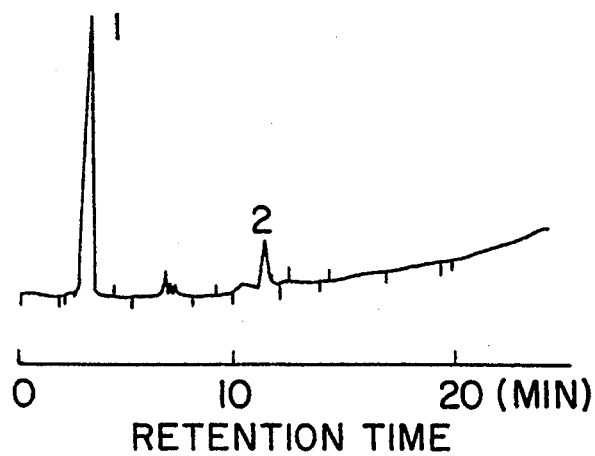
FIG. 2(a)–2(c) show the results of examining disaccharide components of enzyme degradation product.
Figure 2B:
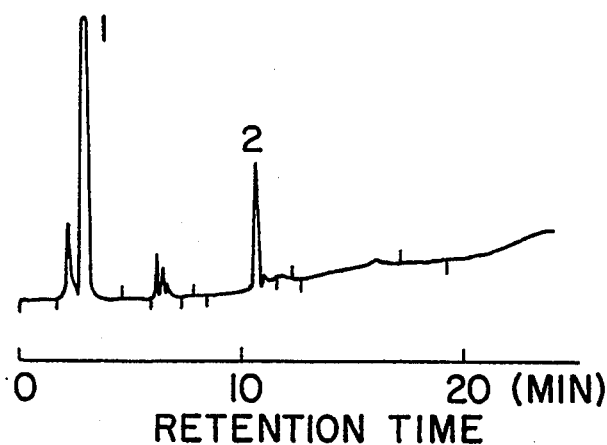
Figure 2C:
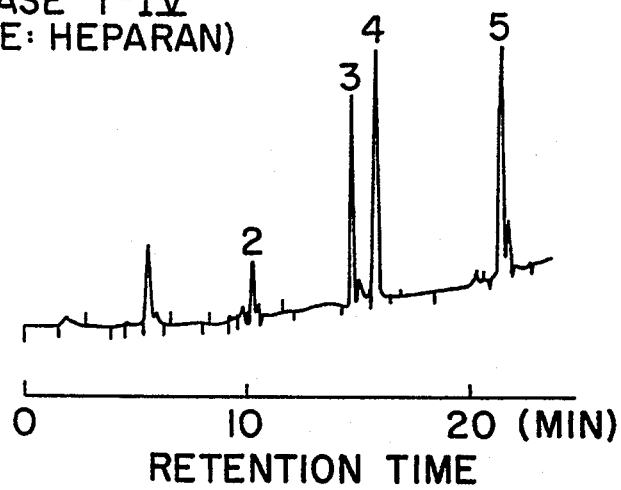

(2) Substrate specificity (FIG. 1–FIG. 2)

Heparitinase T-I and heparitinase T-II do not substantially act on Hep and they mainly act on HS, and unsaturated disaccharides formed as degraded products are non-sulfate compound (hereinafter referred to as "ΔDiHS-OS") and a little amount of uronic acid-glucosamine-N-sulfate (hereinafter referred to as "ΔDiHS-NS"). Heparitinase T-III does not substantially act on Hep and it mainly acts on HS, and unsaturated disaccharides formed as degraded product are ΔDiHS-OS and ΔDiHS-NS. Heparitinase T-IV acts on Hep and HS, and unsaturated disaccharides formed as degraded product are ΔDiHS-NS, uronic acid-glucosamine-N, 6-disulfate (hereinafter referred to as "ΔDiHS-diN, 6S"), uronic acid-2-sulfate-glucosamine-N-sulfate (hereinafter referred to as "ΔDiHS-diU,NS") and uronic acid-2-sulfate-glucosamine-N,6-disulfate (hereinafter referred to as "ΔDiHS-triS").

Figure 3:
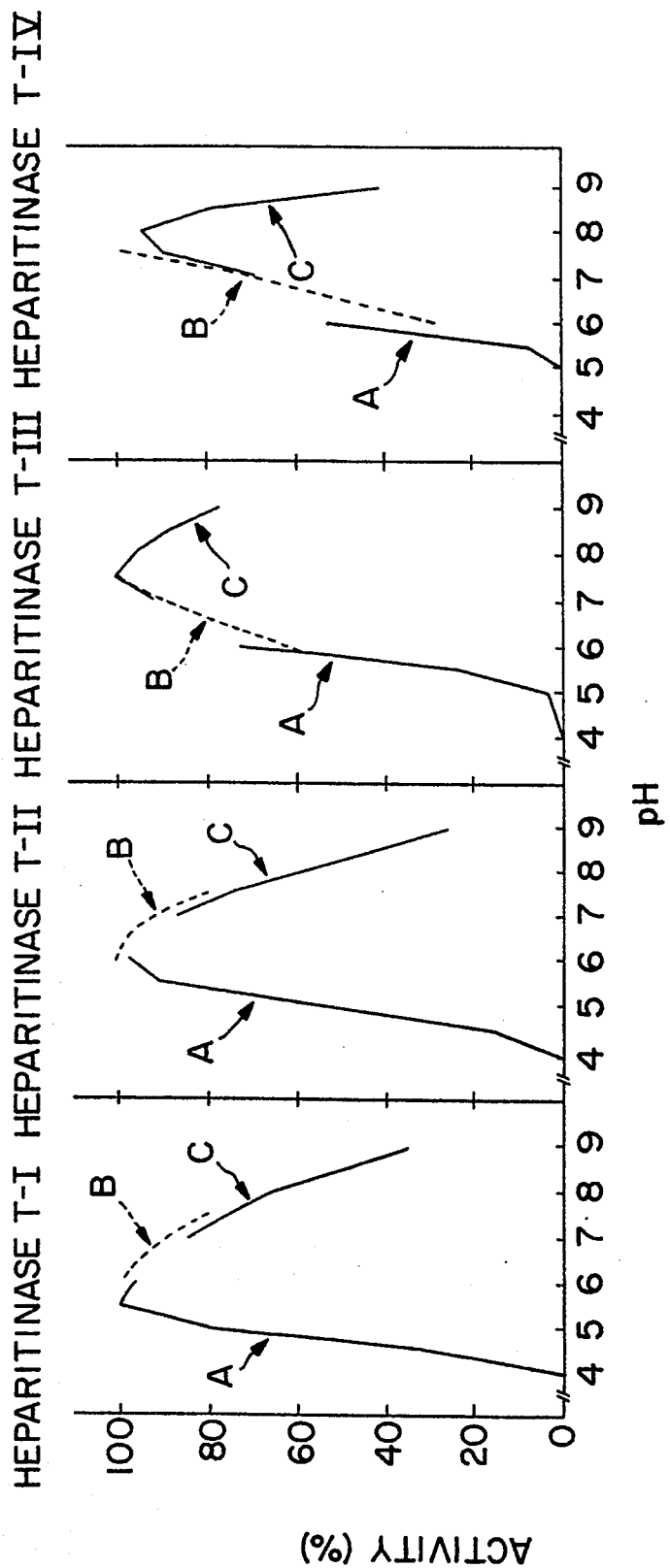
FIG. 3 shows optimum pH.

(3) Optimum pH (FIG. 3)

When the optimum pH of the enzymes of the present invention is examined by the reaction at 45° C. for 10 minutes using 50 mM of sodium acetate buffer, Tris-acetate buffer and Tris-HCl buffer, heparitinase T-I and heparitinase T-II are both pH 5.5 to 6.5, heparitinase T-III is pH 7.0 to 8.0 and heparitinase T-IV is pH 7.5 to 8.0.

Figure 4:
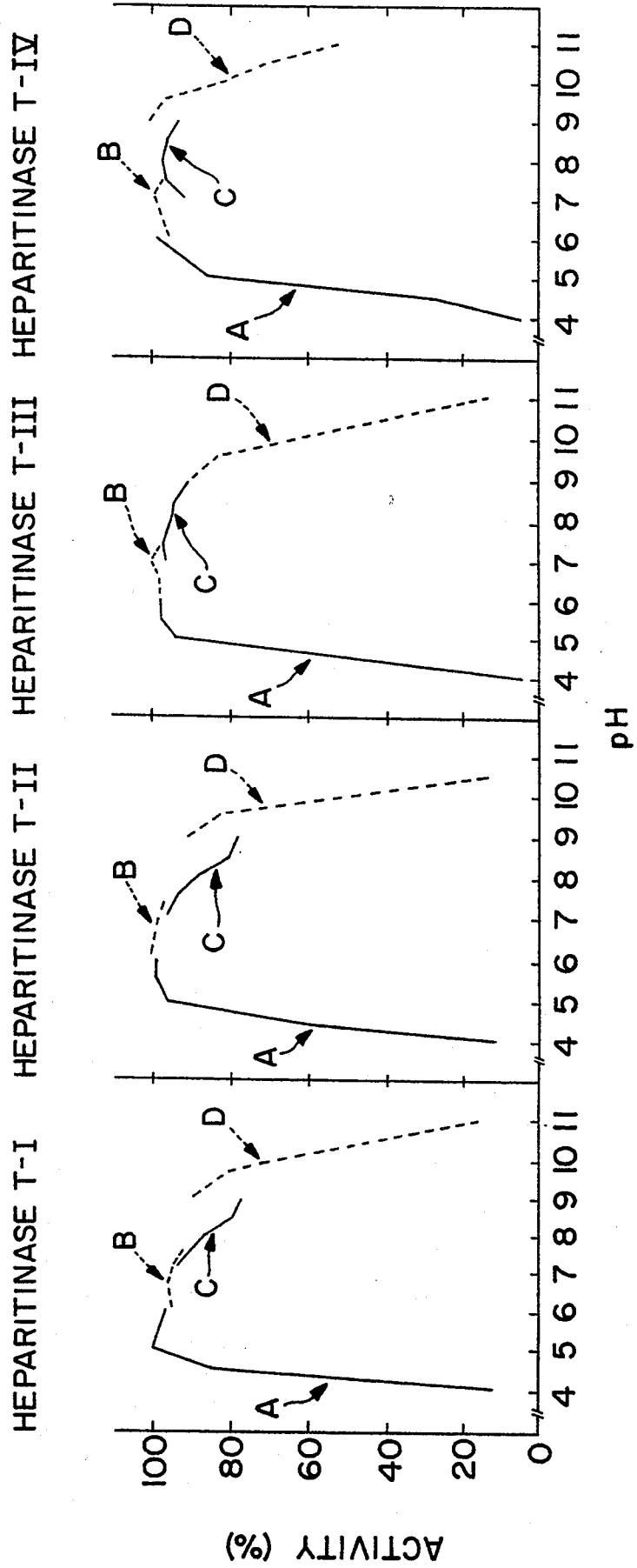
FIG. 4 shows pH stability.

(4) pH stability (FIG. 4)

When the pH stability of the enzymes of the present invention is examined after treating at 37° C. for 30 minutes using 100 mM of sodium acetate buffer, Tris-acetate buffer, Tris-HCl buffer or glycine-NaOH buffer, heparitinase T-I is stable in the range of pH 4.5 to 9.5, heparitinase T-II is pH 5.0 to 9.5, heparitinase T-III is pH 5.0 to 9.5 and heparitinase T-IV is pH 5.0 to 10.0, respectively.

Figure 5:
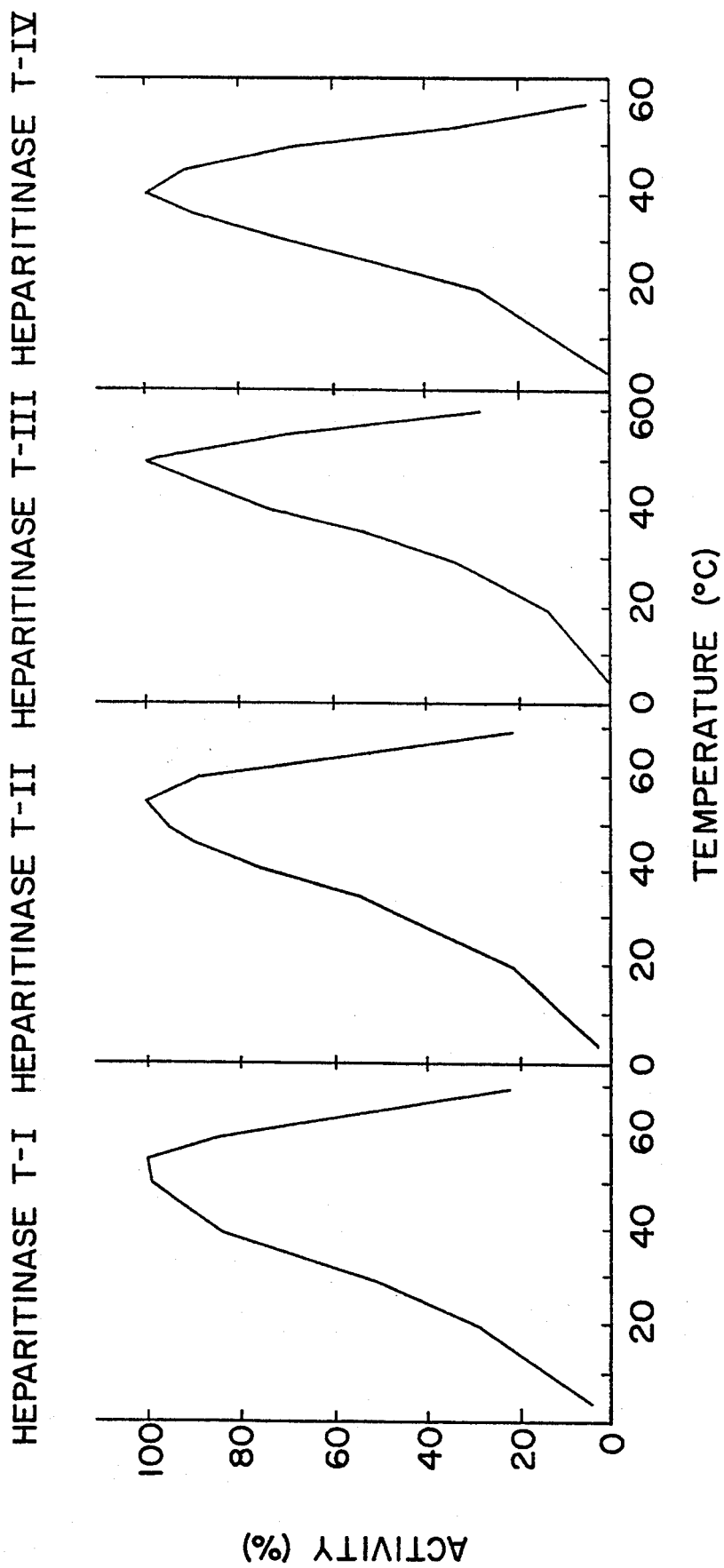
FIG. 5 shows optimum temperature.

(5) Optimum temperature (FIG. 5)

When the optimum temperature of the enzymes of the present invention is examined by the reaction for 10 minutes using 50 mM of Tris-acetate buffer with pH 7.0, optimum temperature of heparitinase T-I and heparitinase T-II are both 55° C., heparitinase T-III is 50° C. and heparitinase T-IV is 40° C.

Figure 6:
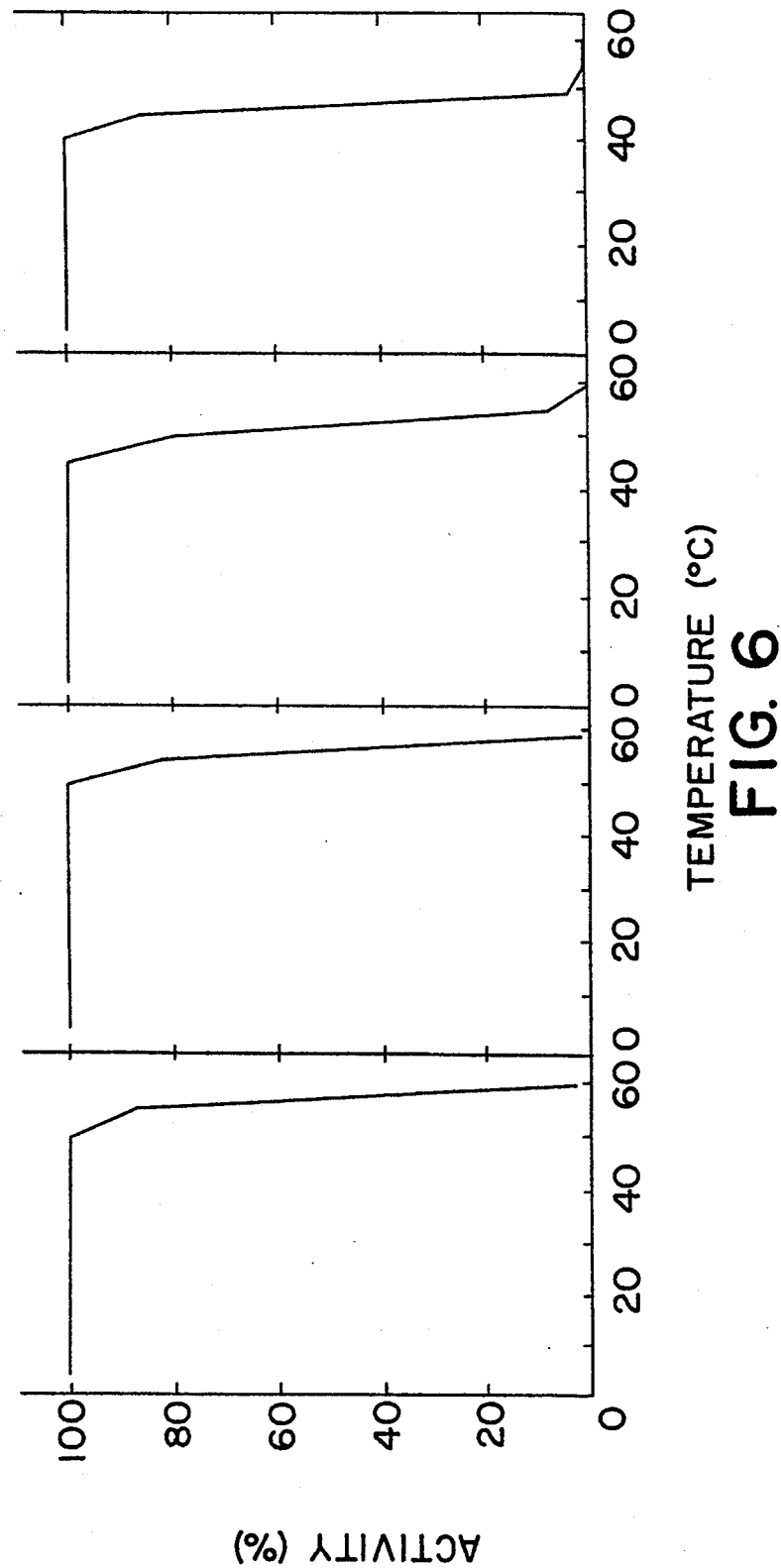
FIG. 6 show heat stability.

(6) Heat stability (FIG. 6)

When the heat stability of the enzymes of the present invention is examined after treating at each temperature for 60 minutes using 50 mM of Tris-acetate buffer with pH 7.0, heparitinase T-I and heparitinase T-II are stable at each 50° C. or lower, heparitinase T-III is 45° C. or lower and heparitinase T-IV is 40° C. or lower, respectively.

(7) Condition of inactivation due to pH, temperature, etc. (FIG. 4 and FIG. 6)

When the activity of the enzymes of the present invention is examined after treating at 37° C. for 30 minutes using 100 mM of sodium acetate buffer, Tris-acetate buffer, Tris-HCl buffer or glycine-NaOH buffer, heparitinase T-I, heparitinase T-II and heparitinase T-III are abruptly inactivated at pH of 4.5 or less and 10.0 or more and heparitinase T-IV is inactivated at pH of 4.5 or less and 10.5 or more, respectively. Also, when the enzymes of the present invention are examined by treating at each temperature for 60 minutes using 50 mM of Tris-acetate buffer with pH 7.0, heparitinase T-I and heparitinase T-II are abruptly inactivated at each 55° C. or higher, heparitinase T-III is inactivated at 50° C. or higher and heparitinase T-IV is inactivated at 45° C. or higher, respectively.

(8) Effect (inhibition and activation) of inorganic ion (Table 1)

Activities of the enzymes of the present invention are activated or inhibited by various kinds of ions. Heparitinase T-I is activated by $Ca^{2+}$, $Co^{2+}$, $Mg^{2+}$ and $Mn^{2+}$, and inhibited by $Zn^{2+}$. Heparitinase T-II is activated by $Ba^{2+}$, $Ca^{2+}Co^{2+}$, $Mg^{2+}$ and $Mn^{2+}$, and inhibited by $Zn^{2+}$. Heparitinase T-III is inhibited by $Zn^{2+}$. Heparitinase T-IV is activated by $Ba^{2+}$, $Ca^{2+}$ and $Mg^{2+}$, and inhibited by $Co^{2+}$ and $Zn^{2+}$.

TABLE 1

| Ion (5 mM) | Heparitinase T-I | Heparitinase T-II | Heparitinase T-III | Heparitinase T-IV |
|---|---|---|---|---|
| Control | 100 | 100 | 100 | 100 |
| $K^+$ | 101 | 103 | 101 | 108 |
| $Na^+$ | 101 | 104 | 101 | 108 |
| $Ba^{2+}$ | 118 | 127 | 99 | 167 |
| $Ca^{2+}$ | 128 | 135 | 105 | 178 |
| $Co^{2+}$ | 140 | 132 | 105 | 13 |
| $Mg^{2+}$ | 134 | 135 | 103 | 137 |
| $Mn^{2+}$ | 145 | 140 | 102 | 97 |
| $Zn^{2+}$ | 55 | 38 | 22 | 0 |
| $SO_4^{2-}$ | 100 | 104 | 102 | 108 |
| $PO_4^{3-}$ | 104 | 107 | 101 | 99 |

The numerical values in the above Table 1 are relative activity values when the control is made as "100".

(9) Molecular weight

Figure 7:
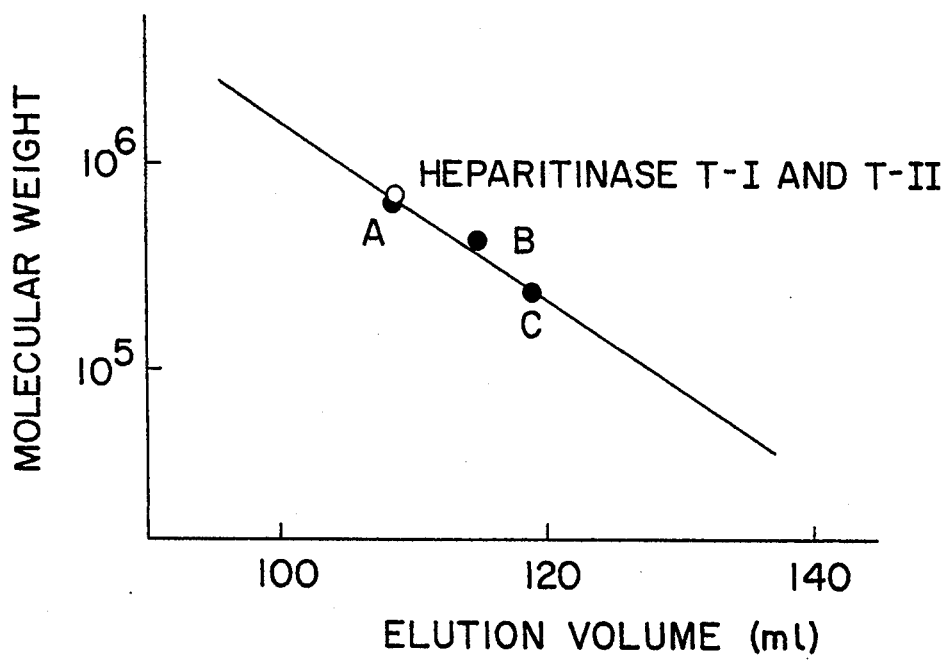
FIG. 7 and FIG. 8 each shows a molecular weight of each enzyme obtained by gel filtration.

When the molecular weights of Heparitinase T-I and Heparitinase T-II are obtained by gel filtration using Toyopearl HW-65 (trade name, available from Toso Co.) column (1.6×90 cm) with 50 mM Tris-acetate buffer (pH 7.0) containing 0.2 M NaCl, the results are shown in FIG. 7. From the results, heparitinase T-I can be calculated to as 710,000±30,000 and heparitinase T-II 710,000±30,000.

Figure 8:
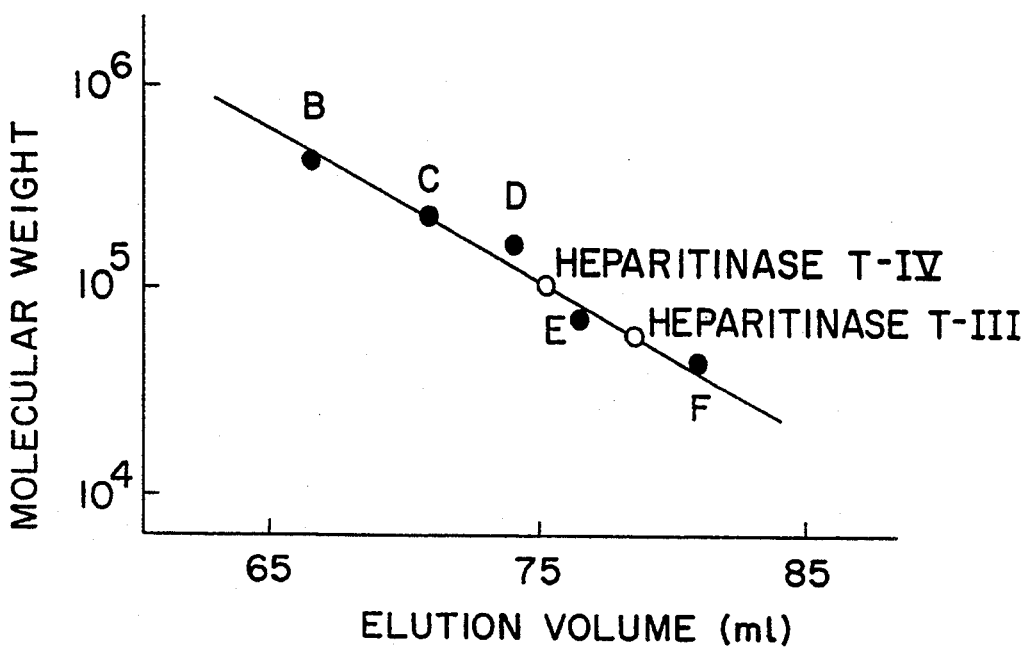

Also, when the molecular weights of Heparitinase T-III and Heparitinase T-IV are obtained by gel filtration using Toyopearl HW-55 (trade name, available from Toso Co.) column (1.6×88 cm) with 50 mM Tris-acetate buffer (pH 7.0) containing 0.2 M NaCl, the results are shown in FIG. 8. From the results, heparitinase T-III can be calculated to as 62,000±5,000 and heparitinase T-IV 107,000±9,000.

In FIG. 7, A is bovine thyroid thyroglobulin (molecular weight: 669,000), B is horse spleen ferritin (molecular weight: 440,000) and C is bovine liver catalase (molecular weight: 232,000). In FIG. 8, B and C are the same as those in FIG.. 7, D is rabbit muscle aldolase (molecular weight: 158,000), E is bovine serum albumin (molecular weight: 67,000) and F is hen egg albumin (molecular weight: 43,000) .

When properties of these four kinds of heparitinases are compared with those of known enzymes, it is confirmed that the above four kinds of heparitinases are novel enzymes having different properties from those of known enzymes by the reasons that heparitinase T-I, heparitinase T-II and heparitinase T-III do not substantially act on heparin but act on heparan sulfate, respectively, and degraded products of which are different from those of known enzymes of bacteria belonging to Flavobacterium, and heparitinase T-IV acts on heparin and heparan sulfate, but degraded products of which are different from those of known enzymes of bacteria belonging to Flavobacterium and optimum temperature and heat stability are different from those of enzymes of bacteria belonging to Bacillus.

EXAMPLES

In the following, the present invention is described in more detail by referring to Examples, but these Examples are not limited the scope of the present invention.

EXAMPLE

In 30000 ml volume of a jar fermentor were charged 20000 ml of a production medium comprising the composition of 0.75% of pepton A (produced by Kyokuto Pharmaceutical Co. ), 0.5% of yeast extract (produced by Kyokuto Pharmaceutical Co. ), 0.5% of sodium heparin (produced by Syntex Co. ), 0.1% of $K_2HPO_4$, 0.02% of $MgSO_4.7H_2O$, 0.1% of NaCl and 0.005% of a defoaming agent ADEKANOL LG109 (trade name, produced by Asahi Denka Kogyo K.K.). After sterilized by steam at 120° C. for 20 minutes, the production medium were inoculated with the 600 ml (inoculum size, 3%) of cultured broth of *Bacillus circulans* HpT 298 which had been shake cultured at 45° C. for 20 hours by inoculating the seed in medium having the same composition (provided that concentration of sodium heparin was 0.2% and no defoaming agent was added) as that of the production medium, and cultivated at 45° C. for 18 hours under aeration (1 v.v.m.) and agitation (300 rpm). The seed was previously prepared by cultivating the strain in heart infusion agar medium (produced by Eiken Kagaku Co. ) at 45° C. for one day.

After completion of cultivation, the culture broth was treated by a continuous centrifugation to collect microbial cells (wet cell weight: 110 g), and a half of the cells was suspended in 300 ml of 0.1 M sodium phosphate buffer (pH 6.8) and crushed by using a sonicator. After crushing, insolubles were removed by centrifugation, ammonium sulfate was added to the resulting supernatant to make 60% saturation, and precipitates formed was collected. The precipitates were dialyzed overnight against 20 mM Tris-acetate buffer with pH 7.0 and dialyzed solution was applied to DEAE-Sephacel (trade name, available from Pharmacia Co.) column (4.2×25 cm) and eluted with the same buffer. The eluate was applied to hydroxyapatite (available from Seikagaku Kogyo K.K.) column (3.2×24 cm), and a linear gradient-elution with 0 to 0.5 M of sodium chloride in the same buffer was performed. When activity of the enzyme was measured by using Hep or HS as substrates, heparitinase T-I was eluted with a passing solution, heparitinase T-II was eluted at around 0.2 M, and heparitinase T-III and heparitinase T-IV were eluted at around 0.4 M. Each fraction was desalted by using an ultrafiltration membrane and then substituted with 50 mM Tris-acetate buffer. Of these, as for both fractions of heparitinase T-I and heparitinase T-II, each was applied to Sephacryl S-300 (trade name, available from Pharmacia Co.) column (3.8×100 cm) and gel filtration was carried out by using 50 mM Tris-acetate buffer containing 0.2 M of sodium chloride. Each of active fractions collected was concentrated and desalted by using an ultrafiltration membrane to obtain an enzyme solution. Also, as for fraction in which heparitinase T-III and heparitinase T-IV were simultaneously eluted, it was applied to sulfated cellulofine (trade name, available from Chisso Corp.) column (3.2×20 cm) and a linear gradient-elution with 0 to 0.3 M of sodium chloride in 50 mM Tris-acetate buffer was performed. Heparitinase T-III was eluted at around 0.1 M and heparitinase T-IV was eluted at around 0.15 M, and each fraction collected was concentrated and desalted by using an ultrafiltration membrane to obtain enzyme solutions, respectively.

Yield of each enzyme:
Heparitinase T-I: 12 U
Heparitinase T-II: 6 U
Heparitinase T-III: 50 U
Heparitinase T-IV: 6 U According to the present invention, novel heparitinase T-I, heparitinase T-II, heparitinase T-III and heparitinase T-IV which degrade heparin or heparan sulfate can be provided.

We claim:

1. A process for producing heparitinase T-I, heparitinase T-II, heparitinase T-III and heparitinase T-IV having the following properties:

(A) action:
each enzyme is a lyase which degrades glucosaminide linkages of heparin or heparan sulfate, and cleaves said linkages to form double bonds between 4-position and 5-position carbon atoms of uronic acids of siad heparin and heparan sulfate, (B) substrate specificity:
heparitinase T-I and heparitinase T-II do not degrade heparin and degrade heparan sulfate, and unsaturated disaccharides formed as degraded products are non-sulfate compound (ΔDiHS-OS) and a small amount of uronic acid-glucosamine-N-sulfate (ΔDiHS-NS); heparitinase T-III does not degrade heparin and degrades heparin sulfate, and unsaturated disaccharides formed as degraded products are non-sulfate compound (ΔDiHS-OS) and uronic acid-glucosamine-N, sulfate (ΔDiHS-NS); heparitinase T-IV degrades heparin and heparin sulfate, and unsaturated disaccharides formed as degraded products are uronic acid-glucosamine-N-sulfate (ΔDiHS-NS), uronic acid-glucosamine-N,6-disulfate (ΔDiHS-diN, 6S), uronic acid-2-sulfate-glucosamine-N-sulfate (ΔDiHS-diU,NS) and uronic acid-2-sulfate-glucosamine-N,6-disulfate (ΔDiHS-tris), (C)pH range at which enzymes have optimum degradation rate:
heparitinase T-I: 5.5 to 6.5 heparitinase T-II: 5.5 to 6.5
heparitinase T-III: 7.0 to 8.0
heparitinase T-IV: 7.5 to 8.0,
(D) pH stability:
heparitinase T-I: 4.5 to 9.5
heparitinase T-II: 5.0 to 9.5
heparitinase T-III: 5.0 to 9.5
heparitinase T-IV: 5.0 to 10.0,
(E) temperature at which the enzymes have the highest degradation activity:
heparitinase T-I: 55° C.
heparitinase T-II: 55° C.
heparitinase T-III: 50° C.
heparitinase T-IV: 40° C.
(F) temperature at which or lower than which the enzyme is stable and at higher than which the enzyme is degenerated due to heat and deactivated:
heparitinase T-I: about 50° C.
heparitinase T-II: about 50° C.
heparitinase T-III: about 45° C.
heparitinase T-IV: about 40° C.
(G) inhibition and activation at ion concentration of 5 mM:
heparitinase T-I: activated by $Ca^{2+}$, $Co^{2+}$, $Mg^{2+}$ and $Mn^{2+}$, and inhibited by $Zn^{2+}$
heparitinase T-II: activated by $Ba^{+2+}$, $Ca^{2+}$, $Co^{2+}$, $Mg^{2+}$ and $Mn^{2+}$, and inhibited by $ZN^{2+}$
heparitinase T-III: inhibited by $Zn^{2+}$
heparitinase T-IV: activated by $Ba^{2+}$, $Ca^{2+}$ and $Mg^{2+}$, and inhibited by $Co^{2+}$ and $Zn^{2+}$
comprising cultivating bacteria belonging to *Bacillus circulana* HpT 298 (FERM BP-3765) and having an ability of producing heparitinase T-I, heparitinase T-II, heparitinase T-III and/or heparitinase T-IV and collecting heparitinase T-I, heparitinase T-II, heparitinase T-III and/or heparitinase T-IV from its culture broth or bacterial cell extract.

2. A *Bacillus circulans* HpT 298 (FERM BP-3765) having an ability to produce at least one of heparitinase T-I, heparitinase T-II, heparitinase T-III and heparitinase T-IV having the following properties:
(A) action:
each enzyme is a lyase which degrades glucosaminide linkages of heparin or heparan sulfate, and cleaves said linkages to form double bonds between 4-position and 5-position carbon atoms of uronic acids of said heparin and heparan sulfate,
(B) substrate specificity:
heparitinase T-I and heparitinase T-II do not degrade heparin and degrade heparan sulfate, and unsaturated disaccharides formed as degraded products are non-sulfate compound (ΔDiHS-0S) and a small amount of uronic acid-glucosamine-N-sulfate (ΔDiHS-NS); heparitinase T-III does not degrade heparin and degrades heparan sulfate, and Unsaturated disaccharideS formed as degraded products are non-sulfate compound (ΔDiHS-0S) and uronic acid-glucosamine-N-sulfate (ΔDiHS-NS); heparitinase T-IV degrades heparin and heparan sulfate, and unsaturated disaccharideS formed as degraded products are uronic acid-glucosamine-N-sulfate (ΔDiHS-NS), uronic acid-glucosamine-N,6-disulfate (ΔDiHS-diN, 6S), uronic acid-2-sulfate-glucosamine-N-sulfate (ΔDiHS-diU,NS) and uronic acid-2-sulfate-glucosamine-N,6-disulfate (ΔDiHS-tris),
(C) pH range at which enzymes have optimum degradation rates:
heparitinase T-I: 5.5 to 6.5
heparitinase T-II: 5.5 to 6.5
heparitinase T-III: 7.0 to 8.0
heparitinase T-IV: 7.5 to 8.0,
(D) pH stability:
heparitinase T-I: 4.5 to 9.5
heparitinase T-II: 5.0 to 9.5
heparitinase T-III: 5.0 to 9.5
heparitinaSe T-IV: 5.0 to 10.0
(E) temperature at which the enzymes have the highest degradation activity:
heparitinase T-I: 55° C.
heparitinase T-II: 55° C.
heparitinase T-III: 50° C.
heparitinase T-IV: 40° C.
(F) temperature at which or lower than which the enzyme is stable and at higher than which the enzyme is degenerated due to heat and deactivated:
heparitinase T-I: about 50° C.
heparitinase T-II: about 50° C.
heparitinase T-III: about 45° C.
heparitinase T-IV: about 40° C.
(G) inhibition and activation at ion concentration of 5 mM:
heparitinase T-I: activated by $Ca^{2+}$, $Co^{2+}$, $Mg^{2+}$ and $Mn^{2+}$, and inhibited by $Zn^{2+}$
heparitinase T-II: activated by $Ba^{2+}$, $Ca^{2+}$, $Co^{2+}$, $Mg^{2+}$ and $Mn^{2+}$, and inhibited by $Zn^{2+}$
heparitinase T-III: inhibited by $Zn^{2+}$
heparitinase T-IV: activated by $Ba^{2+}$, $Ca^{2+}$ and $Mg^{2+}$, and inhibited by $Co^{2+}$ and $Zn^{2+}$.

* * * * *

UNITED STATES PATENT AND TRADEMARK OFFICE
CERTIFICATE OF CORRECTION

PATENT NO. : 5,405,759
DATED : April 11, 1995
INVENTOR(S) : K. MORIKAWA et al

It is certified that error appears in the above-indentified patent and that said Letters Patent is hereby corrected as shown below:

Column 8, line 46, change "siad" to --said-- lines 54 and 58, change "heparin sulfate" to --heparan sulfate--

Column 9, line 26, change "$Ba^{+2+}$" to --$Ba^{2+}$-- line 27, change "$ZN^{2+}$" to --$Zn^{2+}$-- line 32, change "circulana" to --circulans--

Column 10, lines 6 and 10, change "disaccharideS" to --disaccharides-- line 16, change "tris" to --triS--

Column 8, line 65, change "tris" to --triS--

Signed and Sealed this

Twenty-eighth Day of April, 1998

*Attest:*

BRUCE LEHMAN

*Attesting Officer*  *Commissioner of Patents and Trademarks*